United States Patent
Tsujii

(10) Patent No.: US 6,999,552 B2
(45) Date of Patent: Feb. 14, 2006

(54) RADIOGRAPHIC APPARATUS AND METHOD

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/704,036

(22) Filed: Nov. 7, 2003

(65) Prior Publication Data

US 2004/0101096 A1    May 27, 2004

(30) Foreign Application Priority Data

Nov. 18, 2002    (JP)    ............................. 2002-334212

(51) Int. Cl.
  *A61B 6/04*    (2006.01)
  *H05G 1/00*    (2006.01)
(52) U.S. Cl. ........................................ 378/37; 378/208
(58) Field of Classification Search ................ 378/37, 378/89, 8, 39, 50, 55, 196, 198, 208
See application file for complete search history.

(56) References Cited

U.S. PATENT DOCUMENTS

| | | | | |
|---|---|---|---|---|
| 5,553,111 A | * | 9/1996 | Moore et al. | ................. 378/37 |
| 6,292,531 B1 | * | 9/2001 | Hsieh | ........................... 378/37 |
| 6,744,848 B2 | * | 6/2004 | Stanton et al. | ................. 378/55 |
| 6,845,146 B2 | * | 1/2005 | Rick et al. | ..................... 378/37 |

FOREIGN PATENT DOCUMENTS

| | | |
|---|---|---|
| EP | 0 435 837 A1 | 7/1991 |
| FR | 2 685 155 | 6/1993 |
| JP | 55-12429 | 1/1980 |
| JP | 56-11395 | 2/1981 |
| JP | 03-86151 | 4/1991 |
| JP | 03-086154 | 4/1991 |
| JP | 02-504353 | 4/1996 |
| JP | 10-234716 | 9/1998 |
| JP | 2003-126073 | 5/2003 |
| JP | 2003-260046 | 9/2003 |
| WO | WO 96/13211 | 5/1996 |

* cited by examiner

*Primary Examiner*—Edward J. Glick
*Assistant Examiner*—Irakli Kiknadze
(74) *Attorney, Agent, or Firm*—Morgan & Finnegan, LLP

(57) ABSTRACT

A radiographic apparatus includes a radiation generating section, a compression plate to compress an object, and a compression plate moving section which moves the compression plate. The apparatus detects the image of radiation generated by the radiation generating section and transmitted through the compression plate and object, thereby executing radiography. At this time, radiography is executed while keeping the object compressed by the compression plate and causing the compression plate moving section to move the compression plate.

7 Claims, 5 Drawing Sheets

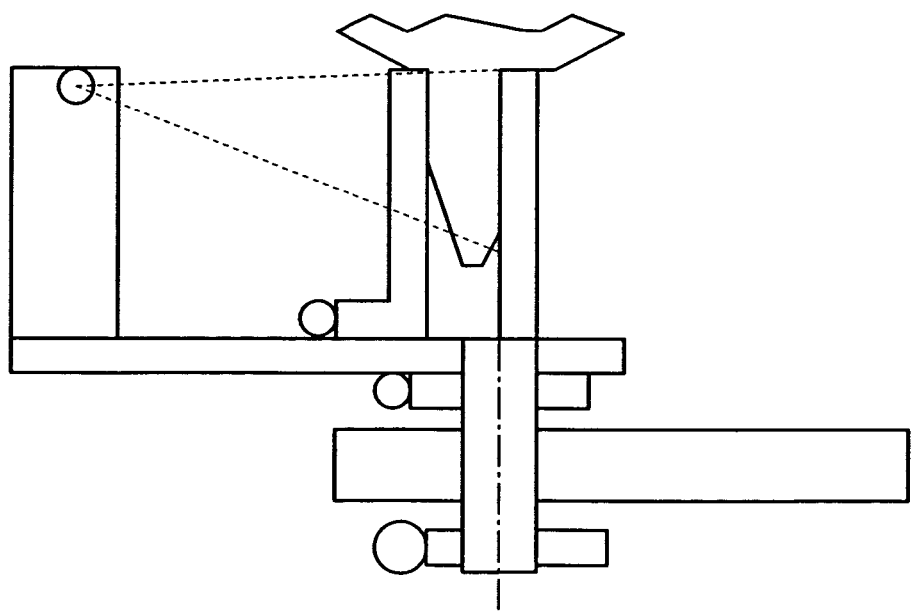
FIG. 3A
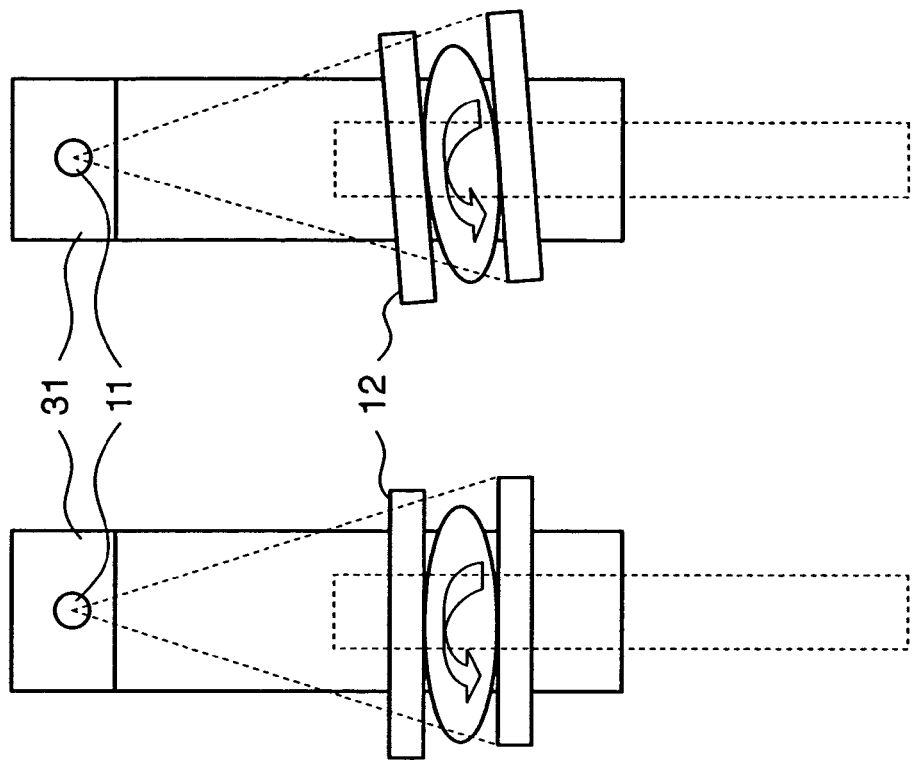
FIG. 3B
FIG. 3C

RADIOGRAPHIC APPARATUS AND METHOD

FIELD OF THE INVENTION

The present invention relates to a radiographic apparatus and method and, more particularly, to a radiographic apparatus and method suitable for mammography.

BACKGROUND OF THE INVENTION

When a certain type of phosphor is irradiated with radiation such as X-rays, α-rays, β-rays, γ-rays, electron rays, or UV rays, part of the radiation energy is accumulated in the phosphor. When this phosphor is irradiated with excitation light such as visible light, the phosphor exhibits stimulated luminescence corresponding to the accumulated energy. A phosphor having such a characteristic is called a cumulative phosphor or stimulated phosphor.

Conventionally, a radiographic image is obtained as an electrical image signal by using a cumulative phosphor. More specifically, radiographic image information of an object such as a human body is temporarily recorded on a cumulative phosphor sheet. The cumulative phosphor sheet is scanned by using excitation light such as a laser beam to generate stimulated luminescent light. The obtained stimulated luminescent light is photoelectrically read to obtain an image signal. A radiographic image information recording/reproduction system which causes a recording material such as a photosensitive material or a display apparatus such as a CRT to output the radiographic image of an object as a visible image on the basis of the image signal is proposed in, e.g., Japanese Patent Laid-Open No. 55-12429 or 56-11395. This method is called computed radiography (CR).

In recent years, a system which obtains the radiographic image of an object by using a semiconductor image sensor having a large area (flat panel detector: FPD) has been developed. This system which can record an image in a very wide radiation exposure area is more advantageous for practical use than a conventional radiographic system that uses a silver halide photo. The procedures of image acquisition in a system of this type are as follows. Dynamic range X-rays in a very wide area are read as an electrical signal by using a photoelectric conversion means. The electrical signal is further converted into a digital signal. The digital signal is processed and output to a recording material such as a photosensitive material or a display apparatus such as a CRT as a visible image. Accordingly, a satisfactory radiographic image can be obtained even when the radiation dose varies to some extent.

Even in mammography, imaging can be executed by using a flat panel detector (FPD) having a pixel size of 50 to 100 μm. In mammography, a compression plate which compresses a breast is used to uniform X-rays that pass through the breast. Various developments are progressing for the compression plate.

Japanese Patent Laid-Open No. 3-86154 discloses a mammographic apparatus having a compression mechanism for manipulating a compression plate that compresses a breast inserted between the compression plate and an imaging table on the X-ray irradiation beam path. The compression mechanism can freely move the compression plate back and forth and/or to the left or right with respect to the subject on a spatial plane that is perpendicular to the X-ray irradiation beam path. The mechanism can also fix and hold the compression plate at a specific moved position.

Japanese Patent Laid-Open No. 2-504353 discloses a mammographic apparatus whose breast holder is constituted by a lower holder and an upper holder. The lower and upper holders can freely displace from each other so that a breast to be imaged is compressed between the lower holder and the upper holder. The frame portion of this apparatus is rotated about or located near an axial line that almost coincides with the central axial line of the breast compressed by the breast holder. Hence, when photo projection or the mode is to be changed, the patient to be imaged need not move or the height position of the apparatus need not be changed.

Japanese Patent Laid-Open No. 10-234716 discloses an X-ray apparatus in which the X-ray generating section and X-ray receiving section are fixed at two ends of a support member. A table is inserted between the X-ray generating section and the X-ray receiving section. The X-ray apparatus has a compression bar driving section which drives a compression bar to compress, e.g., the abdominal part of a patient on the table. The compression bar driving section is supported to be rotatable independently of the rotational direction of the support member. This apparatus executes X-ray imaging of a abdominal part. The X-ray generating section and X-ray receiving section can rotate independently of the compression bar for the abdominal part.

In mammography, a tumor and calcification must be detected. Conventionally, imaging is executed only in two, CC (CranioCaudal) and MLO (MedioLateral Oblique) directions. Hence, a morbid part distribution can hardly be recognized as a stereoscopic vision. If the three-dimensional structure of a tumor and the distribution of a plurality of calcified parts can be recognized in an obtained image, it is expected to be useful for distinction between benign and malignant tumors.

In Japanese Patent Laid-Open No. 3-86154, the compression plate can be moved to suitably align the object and compression plate at the time of X-ray imaging. However, since X-ray imaging is executed in a fixed state, no X-ray image that allows stereoscopic observation can be obtained. In Japanese Patent Laid-Open No. 10-234716, the X-ray generating unit and X-ray receiving section can rotate about the compression bar. However, this apparatus aims at X-ray imaging of a abdominal part. This apparatus is therefore inappropriate for imaging of an object that is deformed by a compression plate as in mammography.

In X-ray imaging such as stereography or rotational DSA (angiography), the three-dimensional distribution of morbid parts in a human body is observed by changing the incident angle of X-rays that become incident on the object. In mammography, however, the motion of the apparatus is restricted because of the relative positional relationship between the apparatus and the human body. For this reason, it is difficult to obtain an image that allows stereoscopic observation by applying the above methods to a mammographic apparatus as in Japanese Patent Laid-Open No. 2-504353. There may also be an idea of applying tomography to mammography. However, the idea is not good because, e.g., the apparatus becomes bulky.

Under the circumstances of the prior arts described above, a radiographic apparatus and method which can execute stereoscopic imaging of an object or acquire three-dimensional information with a simple arrangement are demanded.

SUMMARY OF THE INVENTION

According to one aspect of the present invention, there is provided a radiographic apparatus comprising:

radiation generation means;
a compression plate to compress an object;
movement means for moving the compression plate;
detection means for detecting radiation generated by the radiation generation means and transmitted through the compression plate and the object; and
control means for executing radiography by the radiation generation means and the detection means while keeping the object compressed by the compression plate and causing the movement means to move the compression plate.

According to another aspect of the present invention, there is provided a radiographic method using a radiographic apparatus including radiation generation means, a compression plate to compress an object, movement means for moving the compression plate, and detection means for detecting radiation generated by the radiation generation means and transmitted through the compression plate and the object, comprising:
a control step of executing radiography by the radiation generation means and the detection means while keeping the object compressed by the compression plate and causing the movement means to move the compression plate.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 3A to 3C are views for explaining a situation in which X-ray imaging is executed while rotating the sensor frame in the X-ray imaging apparatus according to the embodiment;

DETAILED DESCRIPTION OF THE PREFERRED EMBODIMENT

A preferred embodiment of the present invention will now be described in detail in accordance with the accompanying drawings.

Figure 1:
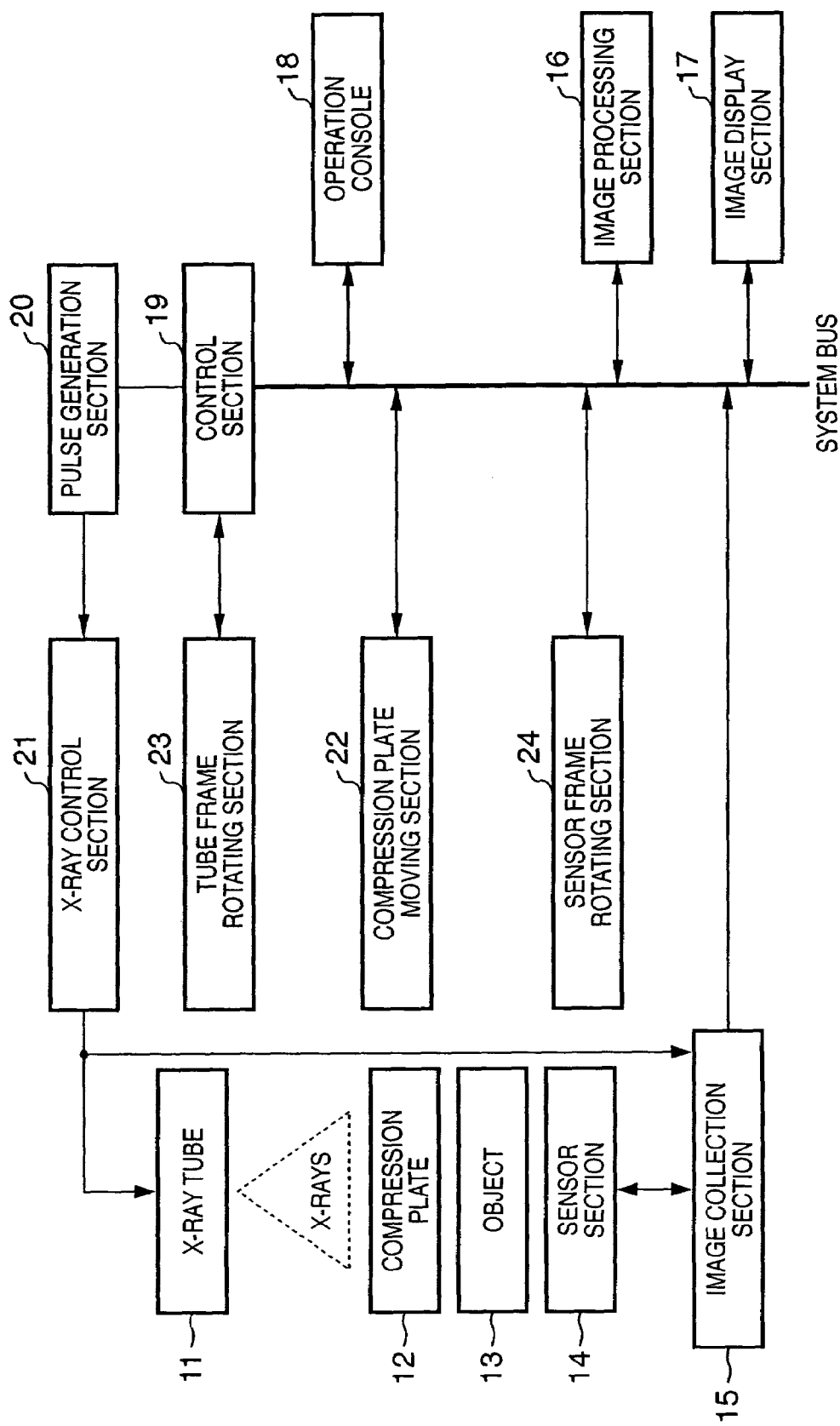
FIG. 1 is a system block diagram showing the arrangement of an X-ray imaging apparatus according to an embodiment.

FIG. 1 is a system block diagram of a digital mammographic apparatus (radiographic apparatus). X-rays emitted from an X-ray tube 11 pass through an object 13 through a compression plate 12 and reaches a sensor section 14. Since this embodiment discloses a mammographic apparatus, a human breast is assumed as the object (also referred to as a target) 13. For the compression plate 12, a material having a predetermined strength and capable of passing X-rays is used. As the sensor section 14, an amorphous silicon sensor or crystal silicon sensor is used. The pixel size is 50 to 100 $\mu m^2$. The outer size of the entire sensor is about 20 cm×25 cm.

The X-rays that have passed through the object 13 become incident on a grid and a phosphor screen (neither are shown) inserted between the object 13 and the sensor section 14. The grid removes scattered X-rays. The phosphor screen changes the X-rays to visible light. The sensor section 14 is driven by an image collection section 15. The sensor section 14 integrates charges in synchronism with the X-ray irradiation timing. Images collected by the image collection section 15 are processed by an image processing section 16 and displayed on an image display section 17. The image processing section 16 comprises preprocessing such as offset correction and gain correction and post processing such as irradiation field extraction, sharpening, and tone conversion to obtain images suitable for diagnosis by a doctor.

The image processing section 16, image display section 17, and a control section 19 can be constituted by computers.

The apparatus is operated from an operation console 18. When mammography is instructed from the operation console 18, the control section 19 implements the following series of functions. Prior to imaging, the object 13 is appropriately arranged between a sensor frame 32 and the compression plate 12. In arranging the breast, it must be confirmed whether movement of the compression plate 12 that moves during imaging will not injure the patient. The start of imaging is instructed from the operation console 18. In accordance with a command from the control section 19, a compression plate moving section 22 operates to move the compression plate 12. The compression plate 12 slidably moves in the lateral direction (the direction perpendicular to the compression direction) of the compression plate 12 so that the breast as the object 13 rolls. When X-rays are emitted in synchronism with the movement of the compression plate 12, and an image is obtained, the stereoscopic distribution or stereoscopic structure of calcification or a tumor can be observed.

On the other hand, a pulse for X-ray irradiation is generated by a pulse generation section 20 in synchronism with the movement of the compression plate 12. When the generated pulse is input to an X-ray control section 21, X-rays are emitted from the X-ray tube 11. The moving amount of the compression plate 12 is about 20 to 30 mm. During this time, three to five mammograms are obtained. Since the X-ray irradiation interval is set to 300 to 500 ms, the entire imaging time is about 1 or 3 sec. In this example, the compression plate 12 is moved only in one direction. However, various moving forms can be applied, and for example, the compression plate may be reciprocally moved.

In the above example, the compression plate 12 is slid in the lateral direction to roll the object 13 in sensing the moving image of the object 13. The compression plate 12 may be moved to change the compression distribution (also referred to as a compression direction) or the strength degree of compression on the object 13. To move the compression plate to change the compression distribution, the compression plate is oscillated about an axis perpendicular to the compression direction. Since the compression plate tilts with respect to the compression direction and compresses the object 13, the compression distribution changes. To change the strength degree of compression, the compression plate is moved in the compression direction to change the compression force on the object 13.

Figure 2C:
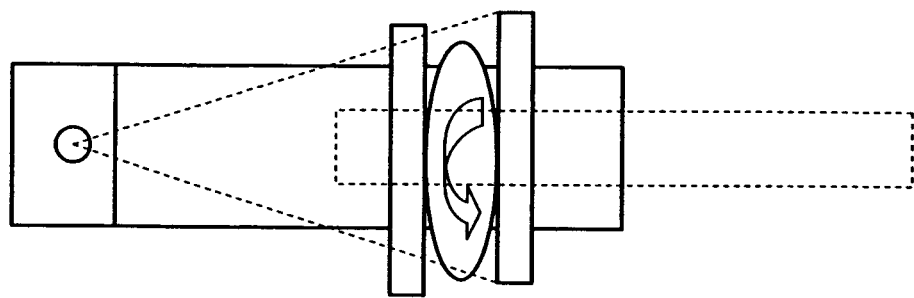
FIGS. 2A to 2C are views for explaining the arrangement of the X-ray imaging apparatus according to the embodiment and a situation in which X-ray imaging is executed while moving the compression plate.
Figure 2B:
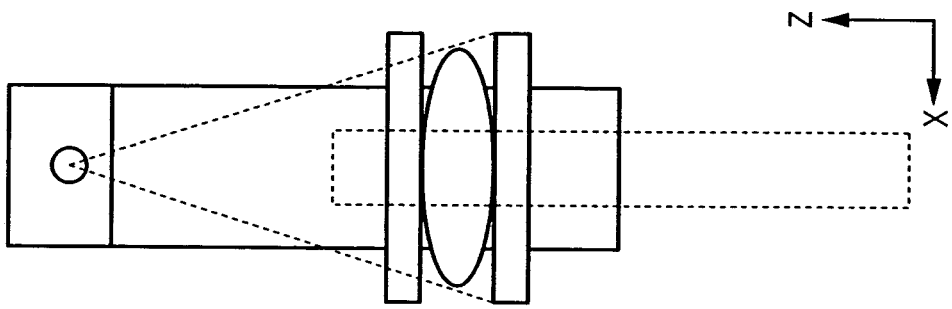
Figure 2A:
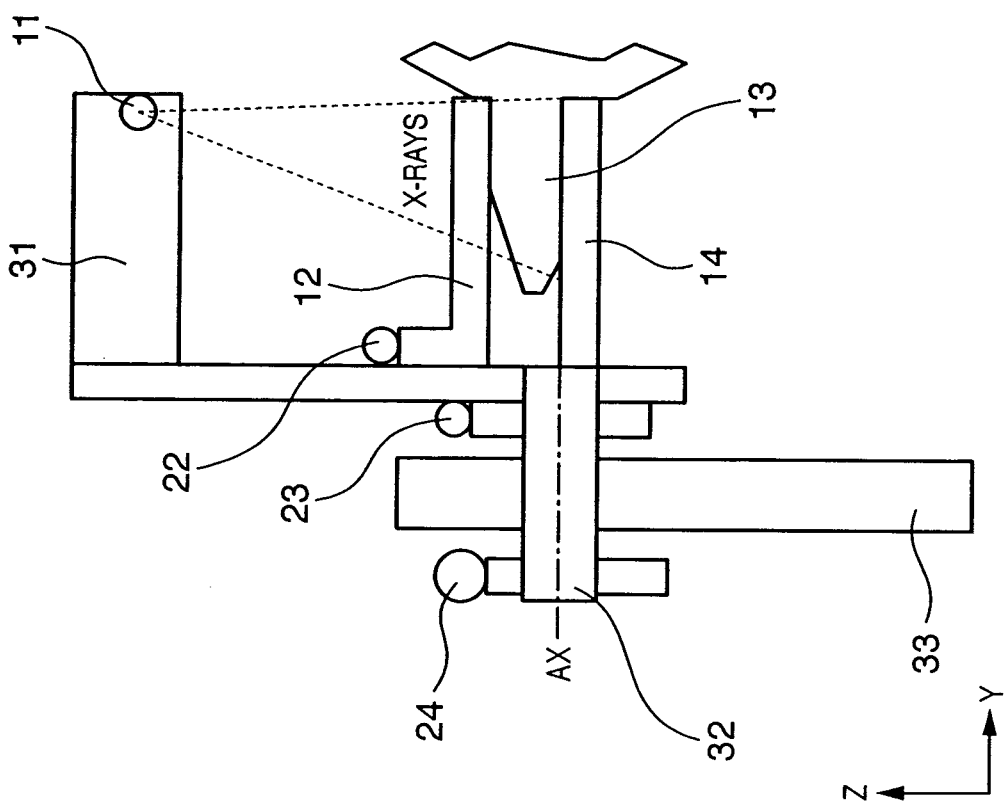

Simultaneously with moving the compression plate 12, the sensor frame 32 or tube frame 31 shown in FIG. 2A can be rotated. Accordingly, object images can be collected from imaging directions in a wide range. This further facilitates stereoscopic observation of morbid parts. The sensor frame 32 and tube frame 31 are rotated by a sensor frame rotating section 24 and tube frame rotating section 23, respectively.

FIGS. 2A to 2C are views showing the mechanism of the X-ray imaging apparatus according to this embodiment. FIG. 2A is a side view of the mammographic apparatus according to this embodiment. The sensor frame 32 is attached to a column 33 to be rotatable about an axis AX. The sensor frame rotating section 24 which rotates the sensor frame 32 about the axis AX is arranged. The sensor section 14, compression plate 12, and tube frame 31 are connected to the sensor frame 32. The tube frame 31 is connected to the sensor frame 32 to be rotatable about the axis AX. The tube frame 31 is rotated by the tube frame rotating section 23 about the axis AX independently of the sensor frame 32. In this example, the sensor frame 32 and tube frame 31 are rotated about the same rotary axis (axis AX) but may be rotated about different axes.

The compression plate 12 is connected to the sensor frame 32 to be movable along two axes (X direction and Z direction). The compression plate 12 can be moved in these directions by the compression plate moving section 22. When the compression plate 12 is moved in the X direction, the object 13 can roll. When the compression plate 12 is moved in the Z direction, the strength degree of compression on the object 13 can be changed. To change the compression distribution, the compression plate 12 is made rotatable (oscillatable) about the Y-axis.

The X-ray tube 11 is attached to the tube frame 31. The object 13 is sandwiched between the sensor frame 32 and the compression plate 12. FIG. 2B is a front view of the X-ray imaging apparatus. This state can be regarded as the imaging start position. Imaging is started from this position. X-ray imaging is executed while moving the compression plate 12 in the X direction, as shown in FIG. 2C. That is, X-ray irradiation is executed a plurality of number of times while rolling the object 13. Images corresponding to the respective irradiation cycles are acquired.

Figure 5:
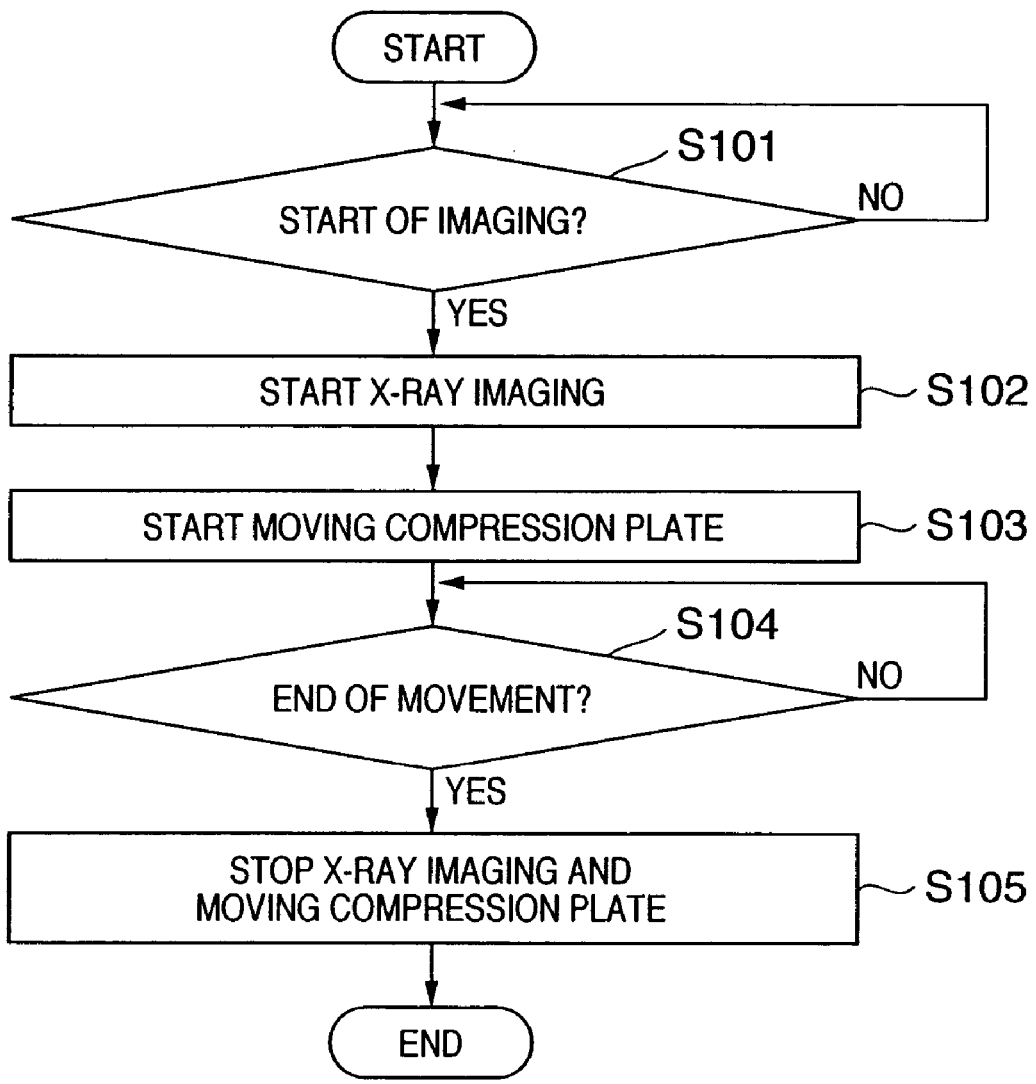
FIG. 5 is a flow chart for explaining the procedures of X-ray imaging according to the embodiment.

FIG. 5 is a flow chart for explaining the operation of the X-ray imaging apparatus according to this embodiment. This processing is implemented by causing the control section 19 to execute a control program stored in a memory (not shown).

First, in step S101, it is determined whether an X-ray imaging start instruction is input from the operation console 18. If YES in step S101, the flow advances to step S102 to instruct the pulse generation section 20 to start X-ray imaging. Upon receiving this instruction, the pulse generation section 20 generates a pulse at an interval of 300 to 500 ms, as described above, and outputs the generated pulse to the X-ray control section 21. Every time the pulse signal from the pulse generation section 20 is received, the X-ray control section 21 drives the X-ray tube 11. The image collection section 15 is also operated in accordance with the pulse signal to acquire an X-ray image.

Simultaneously with the start of X-ray imaging in step S102, movement of the compression plate 12 starts in step S103. More specifically, the control section 19 instructs the compression plate moving section 22 to start moving the compression plate. Upon receiving this instruction, the compression plate moving section 22 moves the compression plate 12 in the X direction shown in FIG. 2B at a predetermined speed.

In steps S102 and S103, X-ray imaging is executed while moving the compression plate 12 (i.e., while rolling the breast as the object 13).

When the compression plate 12 has moved by a predetermined amount, the flow advances from step S104 to step S105 to end X-ray imaging (the pulse generation section 20 is instructed to end X-ray imaging). Simultaneously, movement of the compression plate 12 is ended. The compression plate moving section 22 may monitor the moving amount of the compression plate 12, and the movement may be automatically ended when the compression plate moving section 22 detects the end of movement of the compression plate. In this case, the control section 19 receives a movement end signal from the compression plate moving section 22 and ends X-ray imaging in accordance with this signal.

In the above example, the compression plate 12 is moved in the X direction during X-ray imaging. However, the moving form of the compression plate during X-ray imaging is not limited to this. For example, when the compression plate 12 is moved in the compression direction (Z direction) during X-ray imaging, X-ray imaging can be executed while changing the strength degree of compression on the object 13. When the compression plate 12 is rotated about a rotary axis in a direction (Y direction) perpendicular to the compression direction of the compression plate 12, the compression plate can be tilted with respect to the compression direction. Accordingly, X-ray imaging can be executed while changing the compression distribution on the object 13. As described above, even when the deformation state of the object is changed by changing the compression form, the three-dimensional information of the object can be obtained. Each of the above-described compression plate moving forms may be used independently. Alternatively, some forms may be combined. The compression plate moving forms to be used or a combination thereof may be designated from the operation console 18.

In this embodiment, the compression plate 12 is moved while executing X-ray imaging. In addition, the sensor frame 32 and/or the tube frame 31 is rotated. With this operation, the X-ray incident angle on the object can further largely be changed. Whether the X-ray incident angle should be changed can be set from the operation console 18.

Figures 4B, 4C:
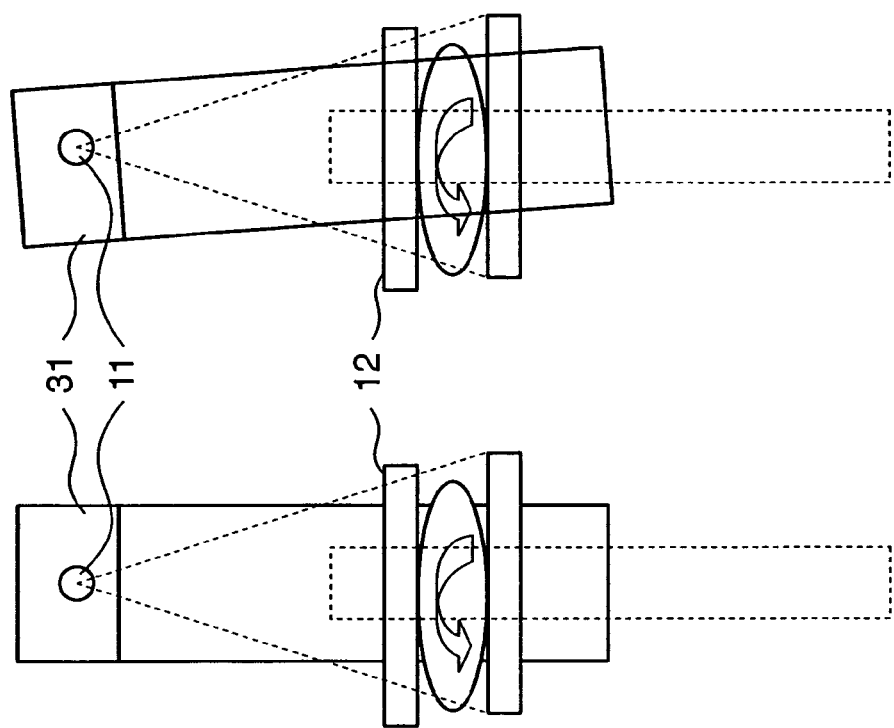
FIGS. 4A to 4C are views for explaining a situation in which X-ray imaging is executed while rotating the sensor frame in the X-ray imaging apparatus according to the embodiment.
Figure 4A:
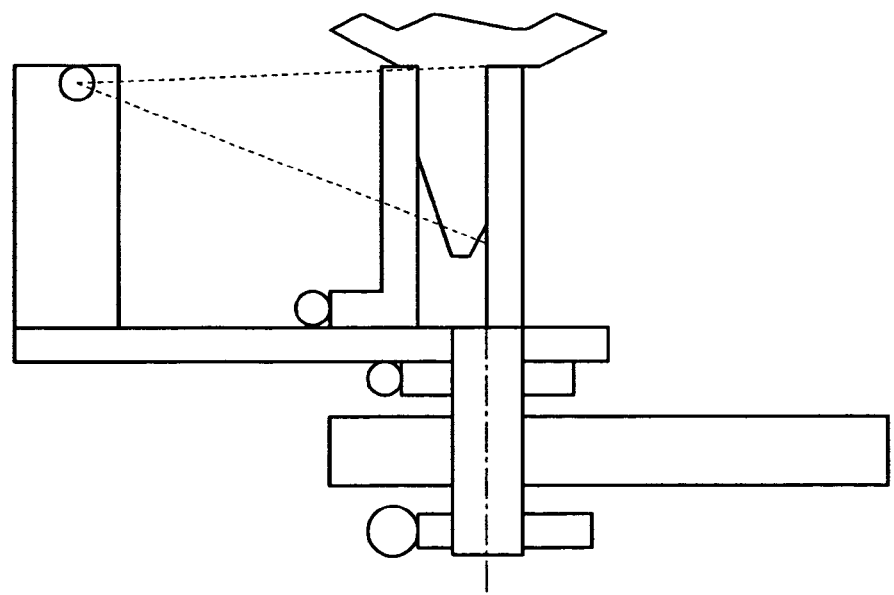

FIGS. 3A to 3C show imaging in which the sensor frame 32 is rotated simultaneously with the movement of the compression plate 12. Referring to FIG. 3C, the sensor frame 32 is rotated. Hence, the change in X-ray incident angle can be made larger than that in only rolling by the movement of the compression plate 12. For this reason, a more effective stereoscopic vision can be obtained (in the arrangement illustrated, if the sensor frame 32 is to be rotated while keeping the tube frame 31 standing still, as shown in FIG. 3C, the tube frame 31 must be rotated in the reverse direction). FIGS. 4A to 4C show imaging in which the tube frame 31 is rotated simultaneously with the movement of the compression plate 12. Referring to FIG. 4C, the tube frame 31 is rotated. Hence, the change in X-ray incident angle can be made larger than that in only rolling by the movement of the compression plate 12, as in FIG. 3C. For this reason, a more effective stereoscopic vision can be obtained.

As described above, according to this embodiment, a large change in stereoscopic visual field (the imaging direction to the object) can be obtained by a small motion of the compression plate 12. Hence, in mammography, images that allow stereoscopic observation can easily be obtained. For this reason, in mammography, images that allow recognition of the three-dimensional structure of a tumor or the three-dimensional distribution of calcified parts, i.e., stereoscopic observation can be obtained. This is useful for distinction between benign and malignant tumors of a breast part of interest.

In the above embodiment, it is important to execute X-ray imaging in a plurality of movement states of the compression plate. The relationship between the compression plate position and the X-ray imaging timing at the time of X-ray imaging or the relative positional relationship between the compression plate and the sensor frame or tube frame at the time of X-ray imaging is not limited to the above-described example. The relationship between the compression plate movement state and the X-ray imaging timing may be a synchronous relationship in which X-ray imaging is executed every time the compression plate is moved by a predetermined amount or an asynchronous relationship. Alternatively, for example, an operation of moving the compression plate 12 by a predetermined amount (e.g., 5 mm), stopping the compression plate, and executing X-ray imaging of one cycle may be repeated a predetermined number of times.

The object of the present invention can also be achieved by supplying a storage medium which stores software program codes for implementing the functions of the above-described embodiment to a system or apparatus and causing the computer (or CPU or MPU) of the system or apparatus to read out and execute the program codes stored in the storage medium.

In this case, the program codes read out from the storage medium implement the functions of the above-described embodiment by themselves, and the storage medium which stores the program codes constitutes the present invention.

As the storage medium for supplying the program codes, for example, a floppy disk (trademark), hard disk, optical disk, magnetooptical disk, CD-ROM, CD-R, magnetic tape, nonvolatile memory card, ROM, or the like can be used.

The functions of the above-described embodiment are implemented not only when the readout program codes are executed by the computer but also when the operating system (OS) running on the computer performs part or all of actual processing on the basis of the instructions of the program codes.

The functions of the above-described embodiment are also implemented when the program codes read out from the storage medium are written in the memory of a function expansion board inserted into the computer or a function expansion unit connected to the computer, and the CPU of the function expansion board or function expansion unit performs part or all of actual processing on the basis of the instructions of the program codes.

As has been described above, according to the present invention, stereoscopic imaging of an object or acquisition of three-dimensional information can be performed with a simple arrangement.

As many apparently widely different embodiments of the present invention can be made without departing from the spirit and scope thereof, it is to be understood that the invention is not limited to the specific embodiments thereof except as defined in the claims.

What is claimed is:

1. A radiographic apparatus comprising:
    a radiation generation unit;
    compression plates to compress an object;
    a movement unit for moving at least one of said compression plates; and
    a detection unit for detecting radiation generated by said radiation generation unit and transmitted through said compression plates and the object,
    wherein said movement unit moves said compression plates such that one of said compression plates is rotated about a rotary axis in a direction perpendicular to the compression direction of said compression plate so that said compression plate is tilted with respect to the other compression plate during radiation detection by said detection unit.

2. The apparatus according to claim 1, further comprising an irradiation direction change unit for changing an irradiation direction of the radiation directed to the object.

3. A radiography method comprising:
    a radiation step of generating radiation using a radiation generation unit;
    a compression step of compressing an object by using compression plates;
    a movement step of moving at least one of said compression plates; and
    a detection step of detecting radiation generated at said radiation step and transmitted through the compression plates and the object, wherein, in said movement step, the compression plates are moved such that one of the compression plates is rotated about a rotary axis in a direction perpendicular to the compression direction of said compression plate so that said compression plate is tilted with respect to the other compression plate during said detection step.

4. A storage medium which stores a program that causes a computer to execute a radiographic method of claim 3.

5. A program that causes a computer to execute a radiographic method of claim 3.

6. A radiographic apparatus comprising:
    a radiation generation unit;
    a compression plate to compress an object;
    a movement unit for moving said compression plate;
    a detection unit for detecting radiation generated by said radiation generation unit and transmitted through said compression plate and the object; and
    a control unit for executing continuous radiography by said radiation generation unit and said detection unit while keeping the object compressed by said compression plate and cause said movement unit to move said compression plate during radiation detection by said detection unit.

7. A radiography method comprising:
    a radiation step of generating radiation by using a radiation generation unit;
    a compression step of compressing an object by a compression plate;
    a movement step of moving the compression plate; and
    a detection step of detecting the radiation transmitted through the compression plate and the object,
    wherein, in said movement step, the compression plate is moved while keeping the object compressed by the compression plate and detecting said radiation during said detection step.

* * * * *